(12) United States Patent
Edel et al.

(10) Patent No.: US 7,715,167 B2
(45) Date of Patent: May 11, 2010

(54) APPARATUS AND METHOD FOR CONTROLLING EXCITATION FREQUENCY OF MAGNETOSTRICTIVE TRANSDUCER

(76) Inventors: Alan Edel, 19 Keren Kayemet St., Petach Tikva (IL) 49372; Julian Edel, 19 Keren Kayemet St., Petach Tikva (IL) 49372; Yitzhak Bloomberg, 37 Brandes St, Petach Tikva (IL) 49294

( * ) Notice: Subject to any disclaimer, the term of this patent is extended or adjusted under 35 U.S.C. 154(b) by 1124 days.

(21) Appl. No.: 11/351,436

(22) Filed: Feb. 13, 2006

(65) Prior Publication Data

US 2006/0188841 A1 Aug. 24, 2006

Related U.S. Application Data

(60) Provisional application No. 60/655,103, filed on Feb. 23, 2005.

(51) Int. Cl.
*H01H 47/00* (2006.01)
*A61C 1/07* (2006.01)
(52) U.S. Cl. ...................... 361/157; 433/119
(58) Field of Classification Search .............. 361/157; 433/119
See application file for complete search history.

(56) References Cited

U.S. PATENT DOCUMENTS

| | | | |
|---|---|---|---|
| 4,060,752 A * | 11/1977 | Walker | 315/244 |
| 4,525,790 A * | 6/1985 | Nakamura | 702/124 |
| 5,151,085 A | 9/1992 | Sakurai et al. | |
| 5,180,363 A | 1/1993 | Idemoto et al. | |
| 5,406,503 A * | 4/1995 | Williams et al. | 702/106 |
| 5,431,664 A * | 7/1995 | Ureche et al. | 606/128 |
| 5,451,161 A | 9/1995 | Sharp | |
| 5,730,594 A | 3/1998 | Sharp | |
| 6,190,167 B1 | 2/2001 | Sharp | |
| 6,241,520 B1 | 6/2001 | Gofman et al. | |
| 6,503,081 B1 | 1/2003 | Feine | |
| 6,623,423 B2 * | 9/2003 | Sakurai et al. | 600/104 |
| 6,819,027 B2 * | 11/2004 | Saraf | 310/316.01 |

* cited by examiner

*Primary Examiner*—Robert DeBeradinis
*Assistant Examiner*—Scott Bauer

(57) ABSTRACT

Apparatus and method for controlling the frequency of the current in the excitation coil of the handpiece of a dental magnetostrictive ultrasonic scaling unit, or similar transducer. A microprocessor continually samples a predetermined function of the current through the excitation coil, and adjusts the frequency for a function maximum, performing coarse and fine frequency adjustments. The function can be proportional to the current, its time-derivative, or combination thereof. A voltage-controlled oscillator is employed, controlled by pulse-width modulation from the microprocessor. The base frequency scan is performed each time the handpiece is energized by the practitioner, assuring automatic optimal frequency adjustment at all times and under all conditions. Apparatus according to the invention does not require transformers, sensing coils, or complex power- or impedance-sensing circuitry, and covers a wide range of resonant frequencies for different insert types. A configuration with multiple handpieces is supported.

15 Claims, 3 Drawing Sheets

APPARATUS AND METHOD FOR CONTROLLING EXCITATION FREQUENCY OF MAGNETOSTRICTIVE TRANSDUCER

The present application claims benefit of U.S. Provisional Patent Application No. 60/655,103 filed Feb. 23, 2005.

FIELD OF THE INVENTION

The present invention relates to controllers for ultrasonic transducers and, more particularly, to the control of the excitation frequency of a magnetostrictive ultrasonic transducer for dental use.

BACKGROUND OF THE INVENTION

The use of a magnetostrictive transducer for an ultrasonic dental device, such as a dental scaler, is well-known and standardized throughout the dental profession. Such devices are characterized by having a handpiece into which a removable insert with a working tip is placed. The handpiece contains an excitation coil which is electrically connected via a cable to a control unit that provides the excitation energy to the coil. The removable insert contains a stack of plates of magnetostrictive material which expands and contracts when subjected to a time-varying magnetic field. A suitable time-varying magnetic field is created by directing a time-varying electrical current through the excitation coil surrounding the inserted tip, and thereby vibrations are induced in the insert and carried to the tip. The vibrating tip is then used by the practitioner in dental work, a non-limiting example of which is to remove calculus from the surface of teeth.

Although the fundamental concept as described above is widely employed in the same basic form, there is considerable variation in the manner by which the excitation current is controlled, in particular the frequency of the time-varying excitation current. The removable insert has a resonant frequency related to the natural acoustic modes of vibration of the magnetostrictive stack contained therein, and it is desirable to excite vibrations within the insert at or near the resonant frequency. Doing so will optimize the vibrational energy in the insert, and will thus optimize the magnitude of the tip vibration for most efficient use in cleaning the teeth.

There are two common sizes of insert, having resonant frequencies of approximately 25 KHz and 30 KHz, respectively. It is thus desirable that the control unit be able to generate time-varying currents at or near these frequencies. A number of different device configurations have been developed to accommodate this requirement.

U.S. Pat. No. 5,151,085 to Sakurai, et al. (herein denoted as "Sakurai") discloses an oscillator for driving an ultrasonic transducer, wherein the oscillator is controlled by feedback from a multi-winding transformer. The transducer of Sakurai, however, is not of the magnetostrictive variety, and does not feature an excitation coil. Instead, Sakurai relies on a rather complex arrangement of inductors, transformers, and amplifiers to detect and match the impedance of the transformer. The handpiece disclosed in Sakurai has no excitation coil; moreover, the controller disclosed in Sakurai is not compatible with magnetostrictive inserts.

Likewise, U.S. Pat. No. 5,180,363 to Idemoto, et al. (herein denoted as "Idemoto") discloses a complex system built around an oscillator featuring impedance-matching transformers and a phase-locked loop for detecting phase mismatch in the feedback signal. As with Sakurai, Idemoto's handpiece lacks an excitation coil; the transducer disclosed in Idemoto is not of the magnetostrictive variety; moreover, Idemoto's controller is incompatible with magnetostrictive inserts.

U.S. Pat. No. 5,451,161 to Sharp (herein denoted as "Sharp '161") discloses a magnetostrictive insert with an excitation coil and a transformer for providing feedback to a transistor oscillator. In the oscillator of Sharp '161, the transistor collector-emitter current flows through the primary winding of the transformer, and also through the excitation coil, which is in series with the transformer's primary. The current induced in the secondary winding of the transformer flows into the base of the transistor, thereby causing the oscillator to oscillate near the resonant frequency of the magnetostrictive insert. The oscillator frequency, however, is not precisely at the resonance point of the insert, because there are additional components involved in the feedback circuit which have energy storage effects. Thus, the oscillator frequency is the resonant frequency of the entire circuit, not that of just the magnetostrictive insert itself. Furthermore, the oscillator of Sharp '161 has a limited range of operation, and normally can accommodate only inserts having a restricted range of resonant frequencies. Therefore, to allow the controller to be utilized with inserts having a resonant frequency of 25 KHz as well as inserts having a resonant frequency of 30 KHz, Sharp '161 provides a switchable capacitance in the transformer's secondary circuit, to provide the oscillator with two frequency ranges. Thus, Sharp '161 requires the practitioner to change the switch setting when changing from one type of insert to the other.

U.S. Pat. No. 5,730,594, also to Sharp (herein denoted as "Sharp '594"), partially overcomes the limitations of Sharp '161 by providing a phase-locked loop oscillator to provide automatic tuning. The transformer feedback of Sharp '161 is not suitable for such an arrangement. In addition, Sharp '594 mentions prior art use of a second coil in the handpiece, adjacent to the excitation coil. The second coil provides the feedback for automatic tuning. Besides the need for an additional coil in the handpiece, Sharp '594 also exhibits some limitations in the automatic tuning of the excitation frequency, and therefore provides manual tuning capabilities to overcome those limitations. It is noted that U.S. Pat. No. 6,190,167, also to Sharp (herein denoted as "Sharp '167"), is a continuation of Sharp '594 and presents no additional material.

U.S. Pat. No. 6,241,520 to Gofman, et al. (herein denoted as "Gofman"), discloses a variation on an oscillator which includes the excitation coil as an integral part of the oscillation circuitry. The inductance of the excitation coil substantially determines the frequency of oscillation of the oscillator. Gofman also features ancillary coils and capacitors ("tank circuits") in the oscillator circuit, so that there are other factors determining the frequency of the oscillation. Thus, as with Sharp '161, as discussed previously, the frequency of oscillation is near, but not exactly at, the resonant frequency of the magnetostrictive insert. Furthermore, Gofman still requires several coils in addition to the excitation coil, thereby incurring additional circuitry complexity and bulk.

U.S. Pat. No. 6,503,081 to Feine (herein denoted as "Feine") discloses the use of a microprocessor to set the frequency of oscillation, such that the power delivered to the excitation coil is maximized. Feine asserts that the microprocessor can be programmed to sense the power input to the excitation coils, perhaps with the use of auxiliary circuitry or components. Feine, however, does not describe how such programming is to be accomplished, nor specifically how to construct such auxiliary circuitry, nor what such auxiliary components might be. But Feine does suggest using voltage-current phase difference measurements or power response slope measurements to determine the maximum power transfer point, in order to set the oscillation frequency to the resonant frequency of the magnetostrictive insert. Although Feine thus suggests a means of reaching the resonant frequency, the requirement for additional power-measurement circuitry imposes further requirements and limitations.

There is thus a widely recognized need for, and it would be highly advantageous to have, a means of automatically adjusting the oscillation frequency of the excitation current of a magnetostrictive insert to be substantially at the resonant frequency thereof, in a simple and direct manner that does not require additional transformers, feedback coils, tank circuits, or complex circuitry. This goal is achieved by the present invention.

SUMMARY OF THE INVENTION

The present invention is of a method and apparatus for controlling the excitation frequency of current flowing through the excitation coil in which a magnetostrictive insert is placed. In the present application, a dental scaler apparatus is used as a non-limiting example of an application for such control method and apparatus. In this non-limiting example, the apparatus is used by a dental practitioner in the cleaning of a patient's teeth. The examples and drawings depicting a dental scaler are understood to be for illustrative purposes only, and do not limit the scope of the present invention, which encompasses other dental and comparable medical uses of ultrasonic devices. The term "magnetostrictive ultrasonic dental device" herein denotes any ultrasonic apparatus intended for dental or medical use which utilizes a magnetostrictive ultrasonic transducer.

It is an objective of the present invention that the frequency be set at an optimal value in a fully automatic manner that does not require any manual adjustment or settings by the practitioner. It is also an objective of the present invention that the frequency be automatically set at an optimal value for a variety of different insert resonant frequencies, over a range at least from 23.5 KHz to 32 KHz, similarly without requiring any settings to be made by the practitioner.

It is moreover an objective of the present invention that the frequency be continually adjusted for optimal performance, and that the frequency be optimally set each time the practitioner energizes the handpiece, such as by means of a foot-operated switch. In this manner, should the practitioner adjust the power to the handpiece, apply additional pressure to the tip, or change the insert, the control apparatus automatically and continually sets the frequency for optimal performance.

It is furthermore an objective of the present invention that the above operating characteristics be attained through relatively simple and inexpensive circuitry and components, preferably utilizing integrated circuitry to the greatest extent possible, and reducing the need for reactive components, such as coils and transformers. In keeping with this, it is an objective of the present invention that multiple handpieces, optionally containing inserts of different resonant frequencies, be accommodated without the need for additional complex circuitry.

Therefore, according to the present invention there is provided a control unit for setting the frequency of the excitation current flowing in an excitation coil of a magnetostrictive ultrasonic dental device, the control unit including: (a) a voltage-controlled oscillator for generating a variable frequency signal; (b) a driver for setting up and regulating the excitation current according to the variable frequency signal; (c) a current sensor in series with the excitation coil, to output a current-sense signal corresponding to the current flowing through the excitation coil; (d) a function block operative to receive the current-sense signal and output a function signal proportional to a predetermined function thereof; and (e) a microprocessor for receiving the function signal and for controlling the voltage-controlled oscillator according to the function signal; wherein the excitation coil is not part of the voltage-controlled oscillator and is not connected directly to the voltage controlled oscillator.

In addition, according to the present invention there is provided a method for controlling the frequency of excitation current flowing in the excitation coil of a magnetostrictive ultrasonic dental device, the method including: (a) providing a current sensor operative to sense the magnitude of the excitation current flowing in the excitation coil and output a current signal proportional to the magnitude; (b) providing a function block operative to output a function signal proportional to a predetermined function of the current signal; (c) providing a controllable frequency-generator means; (d) sensing and storing the value of the function signal; (e) increasing the frequency and sensing the value of the function signal; (f) repeating, if the value of the function signal increases, the increasing the frequency; (g) decreasing the frequency, if the value of the function signal decreases after increasing the frequency; (h) repeating, if the value of the function signal increases, the decreasing the frequency; and (i) locking the frequency, if the value of the function signal decreases after decreasing the frequency.

BRIEF DESCRIPTION OF THE DRAWINGS

The invention is herein described, by way of example only, with reference to the accompanying drawings, wherein.

DESCRIPTION OF THE PREFERRED EMBODIMENTS

The principles and operation of a magnetostrictive ultrasonic dental device control unit according to the present invention may be understood with reference to the drawings and the accompanying description.

Figure 1:
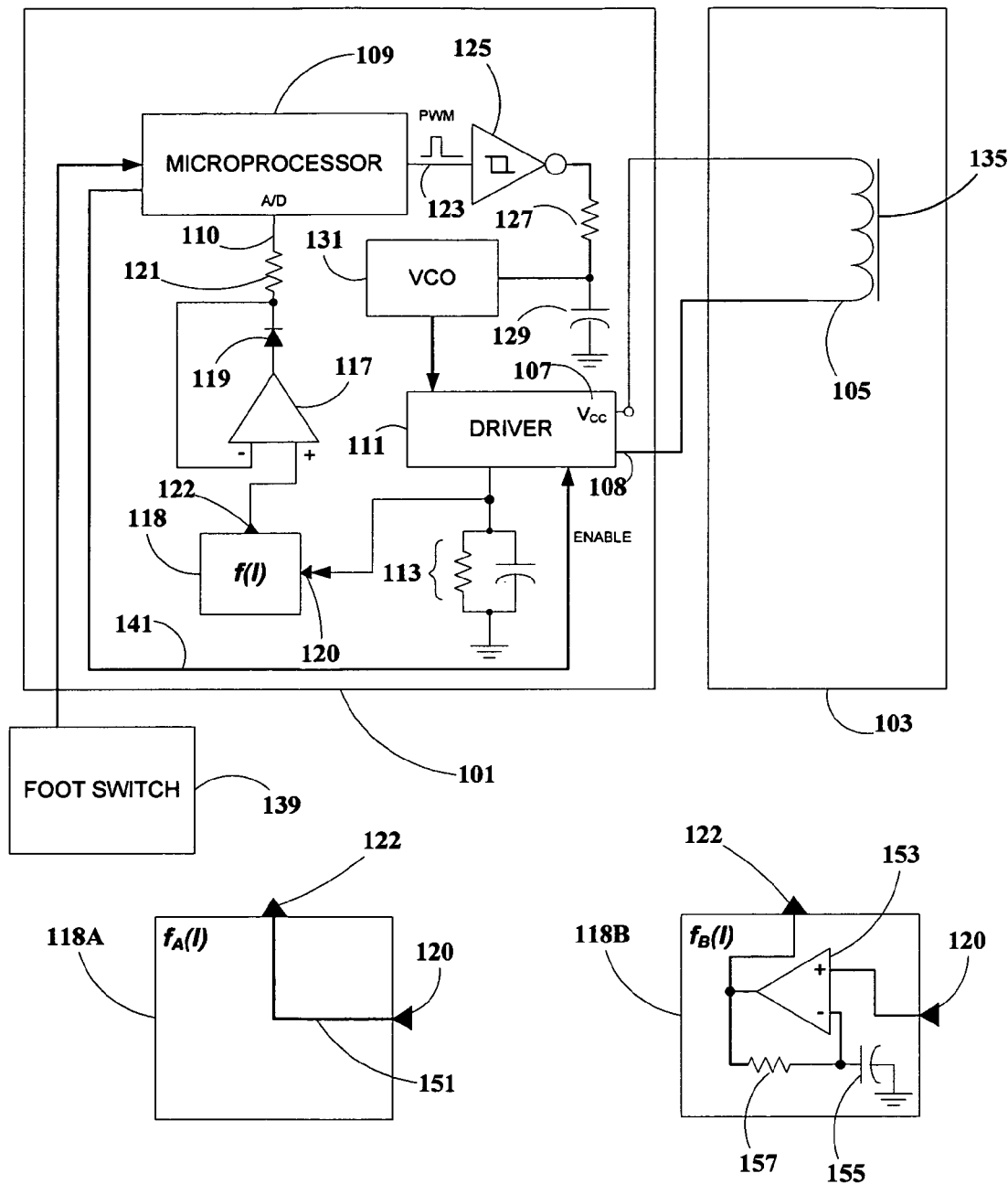
FIG. 1 is a block diagram of a magnetostrictive ultrasonic dental scaler device according to an embodiment of the present invention.

FIG. 1 is a conceptual block diagram of a magnetostrictive dental scaler device according to an embodiment of the present invention. A control unit 101 controls the current through an excitation coil 105 in a separate handpiece 103. A magnetostrictive insert 135 is placed within handpiece 103 within excitation coil 105. (Insert 135 is shown schematically in FIG. 1. In practice, insert 135 is placed physically within the confines of excitation coil 105, such that the tip of insert 135 is exposed and available for cleaning the surfaces of the patient's teeth.)

One end of coil 105 is connected to a driver 111 which sets up a current to flow therein, as follows: Driver 111 includes a voltage source 107, and the other end of coil 105 connects to a return path 108. (Driver 111 is conceptually shown having voltage source 107, whereas in practice, the voltage source can be any suitable voltage point; in practice, driver 111 can be implemented solely with return path 108. As exemplified herein, however, the driver includes the voltage source.)

The input to driver 111 is the output of a voltage-controlled oscillator (VCO) 131, so that driver 111 regulates the flow of current through coil 105 in a time-varying manner at the frequency of voltage-controlled oscillator 131. That is, driver 111 functions as a power amplifier for the output of voltage-controlled oscillator 131.

The input to voltage-controlled oscillator 131 is the voltage across a capacitor 129, which is charged through a resistor 127 by a Schmitt trigger 125 whose input is a pulse-width modulated signal 123 from microprocessor 109. Thus, microprocessor 109 can alter the frequency output from voltage-controlled oscillator 131 by changing the duty cycle of pulse-width modulated signal 123. In an embodiment of the present invention, microprocessor 109 sets the duty cycle of pulse-width modulated signal 123 in order to maximize a function of the current flowing through coil 105. Data about the current is input as follows:

Driver 111 sets up and regulates the current flowing through coil 105 to ground through a current-sensing RC network 113, such that the voltage drop across RC network 113 is proportional to the current flowing through coil 105. This voltage drop represents a current-sense signal, which then goes to an input point 120 to a function block 118. At an output point 122, function block 118 outputs a signal which is proportional to a predetermined function $f$ of the current I which flows through coil 105. In an embodiment of the present invention, the function $f(I)$ is denoted as $f_A(I)$, which is proportional to the current I. In this embodiment, function block 118 is represented by a block 118A, which is schematically shown as having a short circuit 151 between input point 120 and output point 122. In another embodiment of the present invention, the predetermined function $f(I)$ is denoted as $f_B(I)$, which is proportional to dI/dt, the time-derivative of the current I. In this embodiment, function block 118 is represented by a block 118B, which is schematically shown as having an operational amplifier 153, whose non-inverting input receives the signal from input point 120, and whose inverting input receives feedback through a resistor 157 which charges a capacitor 155. In this manner, the output of operational amplifier 153, which goes to output point 122, is proportional to dI/dt.

In an additional embodiment of the present invention, the predetermined function $f$ of the current I contains terms proportional to both the current I itself and the time derivative of the current dI/dt. This embodiment is very general, in that by varying the respective constants of proportionality, the predetermined function can be varied smoothly from being a function of the current I only, to being a function of the time derivative of the current dI/dt only.

The signal from output point 122 goes to the non-inverting input of an operational amplifier 117, whose output goes into an analog input 110 of a microprocessor 109 through a diode 119 and a resistor 121. Microprocessor 109 is equipped with an internal A/D converter which converts the analog input into a digital representation for further processing. Preferably diode 119 and resistor 121 form the feedback loop for operational amplifier 117. In this manner, microprocessor 109 is able to continuously determine the peak value of the predetermined function $f$ of the current flowing through excitation coil 105.

The initiating of ultrasonic vibration is triggered by the action of the practitioner, typically by pressing on a foot-operated switch 139. Foot switch 139 is considered to be either in an "on" state or in an "off" state. In an embodiment of the present invention, the "on" state occurs when foot switch 139 is depressed, and the "off" state occurs when foot switch 139 is not depressed. In another embodiment of the present invention, the "off" state occurs when foot switch 139 is depressed, and the "on" state occurs when foot switch 139 is not depressed. When the practitioner depresses switch 139, microprocessor 109 is signaled to enable driver 111 over a line 141 to allow time-varying current to flow through coil 105. When switch 139 is not depressed, however, microprocessor disables driver 111, also via line 141.

It is noted that according to the present invention, the feedback which controls the frequency of oscillation is solely in connection with the sensed current passing through the excitation coil, and that the excitation coil is not part of the oscillator circuit and does not connect directly with the oscillator circuit.

Figure 2:
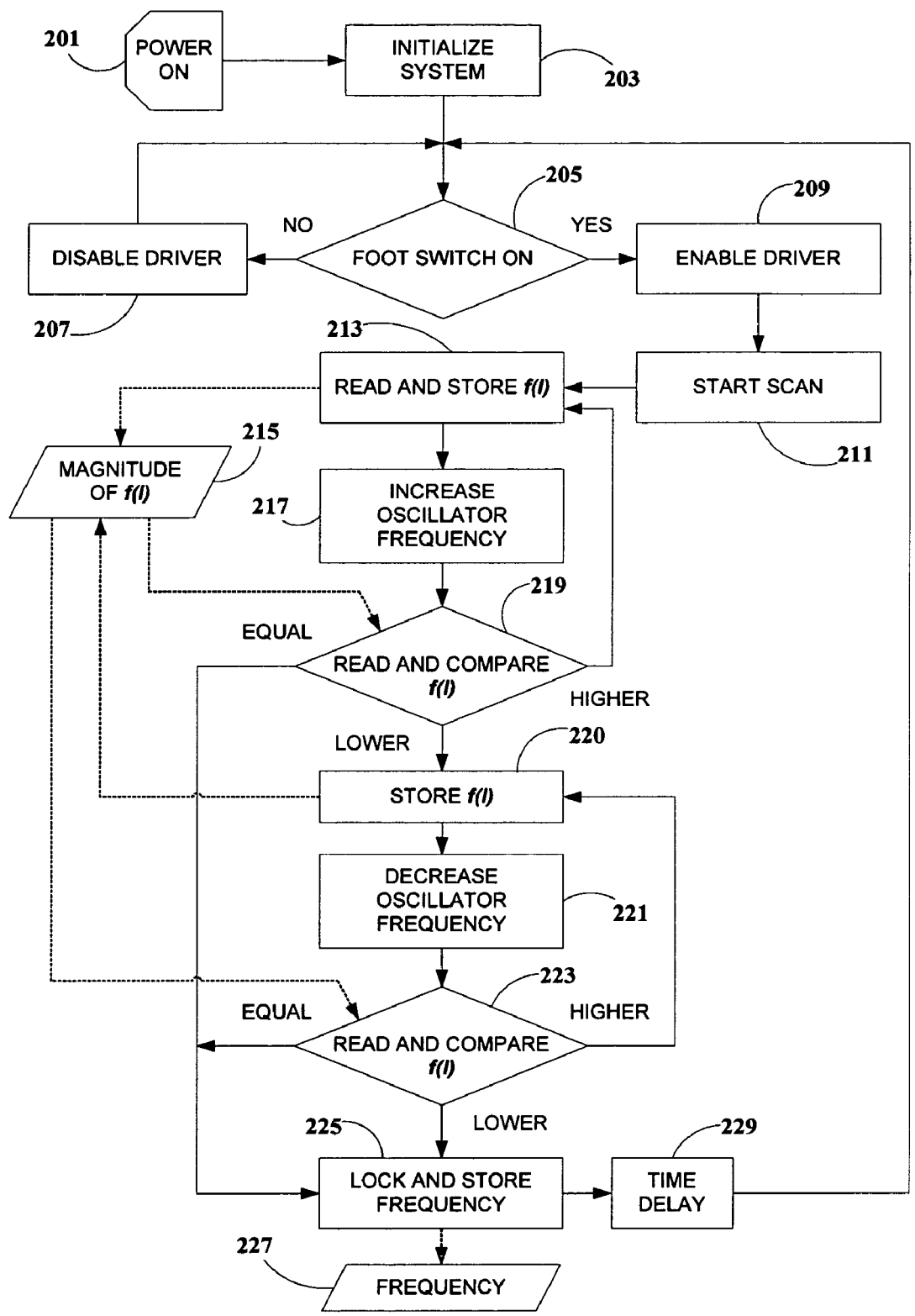
FIG. 2 is a flowchart of a method for controlling a magnetostrictive ultrasonic dental scaler device according to an embodiment of the present invention.

FIG. 2 is a flowchart of a method according to the present invention for setting the frequency of the current flowing through the excitation coil. This method requires having a means of generating a controllable frequency for the excitation current and a means of sensing the magnitude of excitation current. Other required components are referenced to FIG. 1 and the previous discussions. After a power-on operation 201, the control unit is initialized in a step 203. Then, at a decision point 205, the foot switch (switch 139 in FIG. 1) is checked. If the foot switch is not depressed, then the excitation coil driver (driver 111 in FIG. 1) is disabled and decision point 205 is repeatedly checked, as shown. If the foot switch is depressed, then the excitation coil driver is enabled, and the frequency scan is begun in a step 211.

The frequency scan starts with reading and storing the value of the function $f$ of the current in a step 213. The value of the function $f$ of the current is stored in a data element 215. (The mechanism for reading the value of the predetermined function $f$ of the current is described above and illustrated in FIG. 1.) Next, in a step 217, the frequency of the oscillator (voltage-controlled oscillator 131 in FIG. 1) is increased, and at a decision point 219 the value of the actual function $f$ of the current is compared to the stored value in data element 215. If the function $f$ of the current is higher, then step 213 is repeated, which will once again increase the oscillator frequency. If, however, the function $f$ of the current is lower, then the new value of the function $f$ of the current is stored in a step 220, and in a step 221, the oscillator frequency is decreased. That is, if increasing the oscillator frequency leads to an increase in the value of the function $f$ of the current, the oscillator frequency is increased again. If, however, an increase in oscillator frequency leads to a decrease in the value of the function $f$ of the current, the oscillator frequency is decreased.

Similarly, at a decision point 223, the value of the actual function $f$ of the current is compared to the stored value in data element 215. If the function $f$ of the current is higher, then step 220 is repeated, which will once again decrease the oscillator frequency. If, however, the function $f$ of the current is lower, then in a step 225 the frequency is locked and stored in a data element 227. That is, if decreasing the oscillator frequency leads to an increase in the value of the function $f$ of the current, the oscillator frequency is decreased again. If, however, a decrease in oscillator frequency leads to a decrease in the function $f$ of the current, the oscillator frequency is locked and stored.

It is noted that if the function $f$ of the current neither increases nor decreases in the check of decision points 219 and 223, step 225 is performed to store and lock the frequency. Because the values of the function $f$ of the currents are digitized (such as by the A/D conversion of microprocessor 109 in FIG. 1), there is a non-zero probability that there is no change in the function $f$ of the current.

In a step 229, a predetermined time delay is imposed, after which the foot switch state is checked again in step 205. In this manner, the frequency is continually adjusted to achieve maximum value of the function $f$ of the current through the excitation coil. According to an embodiment of the present invention, the scan can be performed at regular time intervals many times per second. This allows apparatus according to the present invention to continually update the frequency to take into account changing conditions. Moreover, if the practitioner interchanges tips during a procedure, a control unit according to the present invention will automatically find the optimum frequency regardless of the operating characteristics of the new insert. In an embodiment of the present invention, the frequency scanning method is held in abeyance when the foot switch is released.

It is noted that in the prior art of Feine, the frequency is scanned and adjusted before the foot switch is depressed, thus setting the frequency under a no-load condition, rather than during actual operating conditions as performed according to the present invention.

In an embodiment of the present invention, the frequency increase in step 217 is a "coarse" (or relatively large) frequency increase, whereas the frequency decrease in step 221 is a "fine" (or relatively small) frequency decrease. In this embodiment, the frequency is first scanned coarsely with increasing frequency, and then when the optimum operating point has been passed, the frequency is scanned finely with decreasing frequency until the optimum operating point is reached. In another embodiment, the frequency is first scanned coarsely with decreasing frequency, and then when the optimum operating point has been passed, the frequency is scanned finely with increasing frequency until the optimum operating point is reached.

Figure 3:
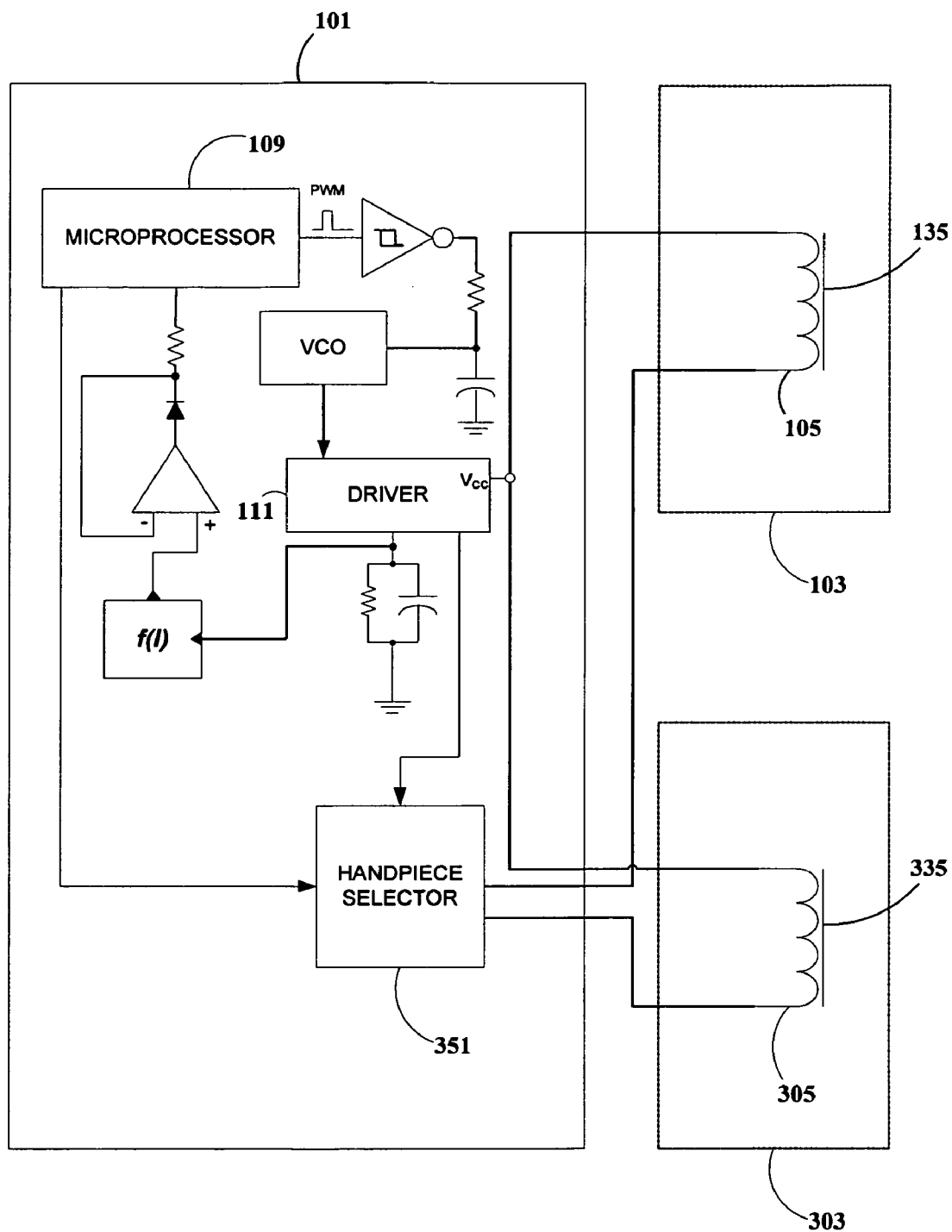
FIG. 3 is a block diagram of a magnetostrictive ultrasonic dental scaler device having multiple handpieces according to an embodiment of the present invention.

FIG. 3 illustrates a configuration having an additional handpiece 303 containing an excitation coil 305 and an insert 335. Instead of driver 111 being connected directly to excitation coil 105 as illustrated in FIG. 1, the output of driver 111 goes to a handpiece selector 351, which connects driver 111 either to coil 105 or to coil 305. Microprocessor 109 controls handpiece selector 351 to make the appropriate selection. More than two handpieces are also possible in a similar way. In this manner, a practitioner can have multiple handpieces with different tips installed for rapid deployment during a procedure.

While the invention has been described with respect to a limited number of embodiments, it will be appreciated that many variations, modifications and other applications of the invention may be made.

The invention claimed is:

1. A control unit for driving an alternating excitation current through an excitation coil of a magnetostrictive ultrasonic dental device and for setting the frequency thereof, the control unit comprising:
    a voltage-controlled oscillator for generating a variable frequency signal;
    a driver for setting up and regulating the excitation current according to said variable frequency signal;
    a current sensor in series with the excitation coil, to output a current-sense signal corresponding to the current flowing through the excitation coil;
    a function block operative to receive said current-sense signal and output a function signal proportional to a predetermined function thereof;
    an electrical arrangement receptive to said function signal and operative to continuously determine a value thereof; and
    a microprocessor for receiving said function signal and for controlling said voltage-controlled oscillator according to said function signal;
    wherein the excitation coil is not part of said voltage-controlled oscillator and is not connected directly to said voltage controlled oscillator and wherein said predetermined function of said current-sense signal contains a term proportional to the time-derivative of said current-sense signal.

2. The control unit of claim 1, wherein said microprocessor is operative to control said voltage-controlled oscillator to maximize said function signal.

3. The control unit of claim 1, wherein said microprocessor is operative to control said voltage-controlled oscillator with increasing frequency.

4. The control unit of claim 1, wherein said microprocessor is operative to control said voltage-controlled oscillator with decreasing frequency.

5. The control unit of claim 1, furthermore comprising a foot switch, having an "on" state and an "off" state, wherein said driver is operative to be enabled and disabled according to the state of said foot switch and wherein said microprocessor is responsive to the state of said foot switch and is operative to control said voltage-controlled oscillator to maximize said function signal in response to said foot switch being in the "on" state.

6. The control unit of claim 1, furthermore comprising a handpiece selector, operative to selectively connect said driver and said current sensor with any one of a plurality of excitation coils within a corresponding plurality of handpieces.

7. The control unit of claim 1, wherein said value of the function signal is proportional to the peak value thereof.

8. A method for controlling the frequency of excitation current flowing in the excitation coil of a magnetostrictive ultrasonic dental device, the method comprising:
    (a) providing a current sensor operative to sense the excitation current flowing in the excitation coil and output a current signal proportional thereto;
    (b) providing an electrical arrangement operative to periodically determine and store values of a function signal that is proportional to a predetermined function of said current signal;
    (c) providing a controllable frequency-generator means;
    (d) storing a value of said function signal;
    (e) increasing the frequency, storing a subsequent value of said function signal and comparing it with a previously stored value, to determine whether there was an increase or a decrease in value;
    (f) repeating step e if there was an increase in value and otherwise performing step g;
    (g) decreasing the frequency, storing a subsequent value of said function signal and comparing it with a previously stored value, to determine whether there was an increase or a decrease in value;
    (h) repeating step g if there was an increase in value and otherwise locking said frequency;
wherein said predetermined function of said current signal contains a term proportional to the time-derivative of said current signal.

9. The method of claim 8, further comprising: locking said frequency, if the value of said function signal remains constant after increasing the frequency; and locking said frequency, if the value of said function signal remains constant after decreasing the frequency.

10. The method of claim 8, wherein said increasing the frequency is performed with a coarse frequency interval and wherein said decreasing the frequency is performed with a fine frequency interval.

11. The method of claim 8, wherein said decreasing the frequency is performed with a coarse frequency interval and wherein said increasing the frequency is performed with a fine frequency interval.

12. The method of claim 8, further comprising: providing a foot switch having an "on" state and an "off" state; performing the method when said foot switch is in said "on" state and holding the method in abeyance when said foot switch is in said "off" state.

13. The method of claim 8, further comprising: waiting a predetermined time delay; and repeating the method.

14. The method of claim 13, further comprising: providing a foot switch, having an "on" state and an "off" state; performing the method when said foot switch is in said "on" state and holding the method in abeyance when said foot switch is in said "off" state.

15. The control unit of claim 8, wherein said value of the function signal is proportional to the peak value thereof.

\* \* \* \* \*